(12) United States Patent
Walsh et al.

(10) Patent No.: US 11,148,136 B2
(45) Date of Patent: Oct. 19, 2021

(54) METHODS AND APPARATUS FOR DRIVING FLOW IN A MICROFLUIDIC ARRANGEMENT

(71) Applicant: OXFORD UNIVERSITY INNOVATION LIMITED, Oxford (GB)

(72) Inventors: Edmond Walsh, Oxford (GB); Alexander Feuerborn, Oxford (GB); Peter Richard Cook, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 291 days.

(21) Appl. No.: 16/326,137

(22) PCT Filed: Aug. 16, 2017

(86) PCT No.: PCT/GB2017/052422
§ 371 (c)(1),
(2) Date: Feb. 15, 2019

(87) PCT Pub. No.: WO2018/033736
PCT Pub. Date: Feb. 22, 2018

(65) Prior Publication Data
US 2020/0129977 A1 Apr. 30, 2020

(30) Foreign Application Priority Data

Aug. 18, 2016 (GB) .................................. 1614139
Aug. 18, 2016 (GB) .................................. 1614146
(Continued)

(51) Int. Cl.
*G01N 35/00* (2006.01)
*G01N 1/00* (2006.01)
(Continued)

(52) U.S. Cl.
CPC ....... *B01L 3/502707* (2013.01); *B01L 3/5088* (2013.01); *B01L 3/50273* (2013.01);
(Continued)

(58) Field of Classification Search
CPC ............. B01L 3/502707; B01L 3/5027; B01L 3/50273; C12M 23/00; G01N 35/00; G01N 1/00; G01N 1/10
See application file for complete search history.

(56) References Cited

U.S. PATENT DOCUMENTS

2005/0064209 A1 3/2005 Haines et al.
2007/0039866 A1* 2/2007 Schroeder ............ C12Q 1/6874
210/265
(Continued)

FOREIGN PATENT DOCUMENTS

EP 2 034 318 A1 3/2009
WO WO-01/07161 A1 2/2001
(Continued)

OTHER PUBLICATIONS

International Search Report and Written Opinion in PCT/GB2017/052422, dated Nov. 29, 2017 (11 pages).

*Primary Examiner* — Brian J. Sines
(74) *Attorney, Agent, or Firm* — Foley & Lardner LLP (57) ABSTRACT

Methods and apparatus for driving flow in a microfluidic arrangement are provided. In one disclosed arrangement, the microfluidic arrangement comprises a first liquid held predominantly by surface tension in a shape defining a microfluidic pattern on a surface of a substrate. The microfluidic pattern comprises at least an elongate conduit and a first reservoir. The area of contact between the substrate and a portion of the first liquid that forms the elongate conduit defines a conduit footprint. The area of contact between the substrate and a portion of the first liquid that forms the first reservoir defines a first reservoir footprint. The size and
(Continued)

shape of each of the conduit footprint and the first reservoir footprint are such that a maximum Laplace pressure supportable by the first liquid in the elongate conduit without any change in the conduit footprint is higher than a maximum Laplace pressure supportable by the first liquid in the first reservoir without any change in the first reservoir footprint. A delivery member having an internal lumen leading to a distal opening through which liquid can be delivered is provided. Liquid is pumped into the microfluidic pattern through the distal opening while the distal opening is held in a delivery position. The delivery position is such that the liquid enters the microfluidic pattern via the elongate conduit and drives a flow of liquid into the first reservoir.

14 Claims, 5 Drawing Sheets

(30) Foreign Application Priority Data

| Aug. 18, 2016 | (GB) | ...................................... 1614150 |
| Aug. 18, 2016 | (GB) | ...................................... 1614153 |
| Aug. 18, 2016 | (GB) | ...................................... 1614157 |
| Mar. 30, 2017 | (GB) | ...................................... 1705118 |

(51) Int. Cl.
*G01N 1/10* (2006.01)
*B01L 3/00* (2006.01)
*C12M 3/06* (2006.01)
*C12M 1/00* (2006.01)

(52) U.S. Cl.
CPC ... *B01L 3/502715* (2013.01); *B01L 3/502784* (2013.01); *C12M 23/16* (2013.01); *C12M 29/14* (2013.01); *B01L 2200/0673* (2013.01); *B01L 2200/0694* (2013.01); *B01L 2200/12* (2013.01); *B01L 2300/047* (2013.01); *B01L 2300/06* (2013.01); *B01L 2300/089* (2013.01); *B01L 2300/0816* (2013.01); *B01L 2300/0867* (2013.01); *B01L 2400/0463* (2013.01); *B01L 2400/0469* (2013.01); *B01L 2400/0475* (2013.01); *B01L 2400/0487* (2013.01); *B01L 2400/088* (2013.01)

(56) References Cited

U.S. PATENT DOCUMENTS

| 2010/0302322 | A1* | 12/2010 | Wang .................... B41J 2/14201 |
| | | | 347/68 |
| 2012/0220497 | A1* | 8/2012 | Jacobson ............... B82Y 30/00 |
| | | | 506/16 |
| 2013/0284956 | A1* | 10/2013 | Kwon .................. F16K 99/0051 |
| | | | 251/65 |
| 2016/0169867 | A1 | 6/2016 | Khine et al. |

FOREIGN PATENT DOCUMENTS

| WO | WO-2005/122672 A2 | 6/2005 |
| WO | WO-2011/097677 A1 | 8/2011 |
| WO | WO-2019/033736 A1 | 2/2018 |

* cited by examiner

METHODS AND APPARATUS FOR DRIVING FLOW IN A MICROFLUIDIC ARRANGEMENT

CROSS REFERENCE TO RELATED APPLICATIONS

The present application is a U.S. national Stage of International Application No. PCT/GB2017/051065 filed on Apr. 18, 2017, which claims the benefit of GB Patent Application Nos. 1614139.2, 1614146.7, 1614150.9, 1614153.3, 1614157.4 all filed on Aug. 18, 2016, GB Patent Application No. 1705117.8 filed on Mar. 30, 2017 and International Application No. PCT/GB2016/053204 filed on Oct. 14, 2016, the entire disclosures of all of which are incorporated herein by reference in their entireties.

The invention relates to driving flow in a microfluidic arrangement.

Manipulation of small volumes of liquids is central to many scientific disciplines, including microbiology, cell biology, biochemistry, and materials science. Microfluidic devices in which liquid flows through channels in polydimethylsiloxane (PDMS) are available but fewer such devices than expected have been incorporated into scientific workflows despite demonstrated advantages of the technology. Various reasons are given. Prototyping PDMS-based devices takes at least a few days and is expensive; it also typically requires specialized equipment, a clean room, and advanced training. Once made, devices are usually dedicated to one application, and access to most points in them is limited. Moreover, untreated PDMS has poor biological and chemical compatibility because it leaches toxins and reacts with organic solvents. Air bubbles in conventional devices also present numerous operational challenges: they unbalance flows, damage incorporated cells, and trigger molecular aggregation at air-fluid interfaces.

Driving flow through such devices is difficult because it is necessary to provide sealing arrangements between channels of the device and external pumping apparatus. The sealing arrangements are typically small and difficult to manipulate, as well as being unreliable. Experiments can be compromised due to contamination, leakage, bubbles and/or unpredictable flow rates. Fluid can only be injected and extracted at specific points in the device, limiting flexibility.

There is interest in providing flows which imitate conditions within humans or animals, for example when performing experiments on living cells. It is therefore desirable to provide a pulsatile flow. Known apparatus for this purpose can be expensive and/or complex to implement.

It is an object of the invention to provide improved methods and apparatus for driving flow in microfluidic arrangements.

According to an aspect of the invention, there is provided a method of driving flow in a microfluidic arrangement, wherein the microfluidic arrangement comprises a first liquid held predominantly by surface tension in a shape defining a microfluidic pattern on a surface of a substrate, the microfluidic pattern comprising at least an elongate conduit and a first reservoir; the area of contact between the substrate and a portion of the first liquid that forms the elongate conduit defines a conduit footprint; the area of contact between the substrate and a portion of the first liquid that forms the first reservoir defines a first reservoir footprint; the size and shape of each of the conduit footprint and the first reservoir footprint are such that a maximum Laplace pressure supportable by the first liquid in the elongate conduit without any change in the conduit footprint is higher than a maximum Laplace pressure supportable by the first liquid in the first reservoir without any change in the first reservoir footprint; and the method comprises: providing a delivery member having an internal lumen leading to a distal opening through which liquid can be delivered; and pumping liquid into the microfluidic pattern through the distal opening while the distal opening is held in a delivery position, the delivery position being such that the liquid enters the microfluidic pattern via the elongate conduit and drives a flow of liquid into the first reservoir.

Thus, a method is provided in which flow is driven in a microfluidic arrangement without solid walls. Surface tension is used instead of solid walls to hold a first liquid in a desired microfluidic pattern. Microfluidic patterns can be formed in this way in seconds in much the same way as writing freehand with a pen. Just as any imaginable pattern can be drawn on a piece of paper, any microfluidic pattern can be created by moving an element emitting the first liquid over the substrate. Edges of elements of the microfluidic pattern such as the conduit and the first reservoir are pinned by surface tension (which may also be referred to as interfacial tension). Because the substrate does not have to be processed in the same way as PDMS to provide channels, the substrate can be made from materials of proven biocompatibility, such as the polystyrene/glass dishes that biologists commonly use.

Unlike PDMS-based devices, the delivery member that pumps liquid into the microfluidic arrangement can be inserted freely at any point in the microfluidic pattern. The connection between the delivery member and the microfluidic arrangement is self-sealing. A seal is automatically established when the delivery member is inserted and automatically closes when the delivery member is removed. Various different pumping modes can therefore be selected without having to build new devices. The microfluidic pattern itself can even be redesigned, for example by cutting through conduits (which self seal) or by joining different conduits together, which provides further flexibility. Furthermore, the risk of contamination is reduced or eliminated, particularly where a second liquid is provided that covers the microfluidic pattern from above, and there are no issues with seal failure or leakage. If bubbles of gas arise they will be forced up and out of the microfluidic pattern by buoyancy forces, thereby eliminating also the negative effects of bubbles that are regularly encountered in PDMS-based devices.

The first liquid is confined by fluid walls which means that the walls can morph during fluid flow. This presents potential limitations to how flow can be driven actively through the microfluidic pattern. If the fluid walls morph in a way which prevents desired pressure gradients from being established, it will not be possible to achieve desired flow rates through the microfluidic pattern. The inventors have recognised that a wider variety of flow rates can be achieved by pumping liquid into the microfluidic pattern at particular locations: namely, into elongate conduits between reservoirs or leading to reservoirs, rather than into reservoirs themselves. Elongate conduits are able to support higher maximum Laplace pressures than reservoirs that are wider than the elongate conduits (due to the higher curvature that is possible in the conduit compared to the reservoir). Pumping into the elongate conduits therefore allows higher pressure gradients and higher corresponding pumping rates through conduits.

In an embodiment, the delivery position is such that the delivery member would not be in contact with the elongate conduit in the absence of any flow of liquid out of the distal opening, and wherein the liquid is pumped into the elongate conduit via a liquid bridge formed between the distal opening and the elongate conduit by a flow of liquid out of the distal opening. This feature reduces the need for highly precise positioning of the delivery member. Effective pumping of liquid into the microfluidic arrangement can be achieved for a range of different positions of the delivery member, optionally including both positions at which the distal opening would be within the first liquid in the absence of pumping and positions at which the distal opening would not be within the first liquid in the absence of pumping. Manual positioning of the delivery member is therefore facilitated. Automation of movement of the delivery member can be implemented more cheaply and/or reliably.

According to an alternative aspect of the invention, there is provided a method of driving flow in a microfluidic arrangement, wherein the microfluidic arrangement comprises a first liquid held predominantly by surface tension in a shape defining a microfluidic pattern on a surface of a substrate, the microfluidic pattern comprising at least an elongate conduit and a first reservoir; the method comprises providing a delivery member having an internal lumen leading to a distal opening through which liquid can be delivered, and pumping liquid into the microfluidic pattern through the distal opening while the distal opening is held in a delivery position; and the pumping of the liquid is such that during a period of uninterrupted flow out of the distal opening an unstable liquid bridge is periodically formed in a cyclical process comprising growth of a globule of liquid at the distal opening, contact of the globule with the first liquid defining the microfluidic pattern to establish the liquid bridge, and subsequent collapse of the liquid bridge, thereby providing a pulsatile flow, as a result of a pulsatile pressure generated by the cyclical process, of liquid into the microfluidic pattern.

Thus, a method is provided in which the advantages associated with microfluidic arrangements without solid walls are achieved and in which a reliable pulsatile flow can be achieved in a simple and repeatable manner. The pulsatile flow is achieved without requiring sophisticated pumping apparatus. The liquid can simply be pumped continuously, for example at a constant rate of flow. The pulsatile flow is provided by the cyclical making and collapsing of the liquid bridge providing a cyclic pressure within the conduit to drive flow.

In an embodiment, the microfluidic arrangement further comprises a second liquid in direct contact with the first liquid and covering the microfluidic pattern. The second liquid isolates the first liquid from the surrounding atmosphere, thereby further reducing the risk of contamination of the microfluidic pattern and/or preventing evaporation of the first liquid. In an embodiment, the delivery position of the delivery member is always below an upper interface of the second liquid.

In an embodiment, the second liquid is denser than the first liquid. This modifies how hydrostatic pressure contributes to driving flow through the microfluidic arrangement and can help maintain more constant flow rates. For example, as reservoirs grow in size due to flow of liquid into them, the Laplace pressure will typically increase as the radii of curvature of the reservoirs decrease. This would normally increase the pressure in the reservoirs and therefore tend to reduce the maximum rate at which liquid can be made to flow into them. With a denser second liquid this effect is countered by a reduction in the hydrostatic pressure as the height of liquid above the reservoirs diminishes.

In an embodiment, at least a selected portion of the outer surface of the delivery member proximate to the distal opening is configured such that a surface energy density is higher in respect of contact with the first liquid than in respect of contact with the second liquid. Configuring the delivery member in this way helps to reduce unwanted wetting of the outer surface of the delivery member by liquid being pumped into the microfluidic pattern. This is particularly desirable where a liquid bridge is being used to make the connection, for example to provide pulsatile flow, where it is important to be able to form a globule of predictable geometry at the distal opening.

In an alternative embodiment, at least a selected portion of the outer surface of the delivery member proximate to the distal opening is configured such that a surface energy density is lower in respect of contact with the first liquid than in respect of contact with the second liquid. Configuring the delivery member in this way helps to provide efficient insertion and sealing of the delivery member into the microfluidic pattern.

According to an alternative aspect of the invention, there is provided an apparatus for driving flow in a microfluidic arrangement, comprising: a microfluidic arrangement comprising a first liquid held predominantly by surface tension in a shape defining a microfluidic pattern on a surface of a substrate, the microfluidic pattern comprising at least an elongate conduit and a first reservoir, wherein the area of contact between the substrate and a portion of the first liquid that forms the elongate conduit defines a conduit footprint; the area of contact between the substrate and a portion of the first liquid that forms the first reservoir defines a first reservoir footprint; and the size and shape of each of the conduit footprint and the first reservoir footprint are such that a maximum Laplace pressure supportable by the first liquid in the elongate conduit without any change in the conduit footprint is higher than a maximum Laplace pressure supportable by the first liquid in the first reservoir without any change in the first reservoir footprint; a pumping mechanism comprising a moveable delivery member having an internal lumen leading to a distal opening through which liquid can be delivered; and a control system configured to control the pumping mechanism such that liquid is pumped into the microfluidic pattern through the distal opening while the distal opening is held in a delivery position, the delivery position being such that the liquid enters the microfluidic pattern via the elongate conduit and drives a flow of liquid into the first reservoir.

According to an alternative aspect of the invention, there is provided an apparatus for driving flow in a microfluidic arrangement, comprising: a microfluidic arrangement comprising a first liquid held predominantly by surface tension in a shape defining a microfluidic pattern on a surface of a substrate, the microfluidic pattern comprising at least an elongate conduit and a first reservoir; a pumping mechanism comprising a moveable delivery member having an internal lumen leading to a distal opening through which liquid can be delivered; and a control system configured to control the pumping mechanism such that during a period of uninterrupted flow out of the distal opening an unstable liquid bridge is periodically formed in a cyclical process comprising growth of a globule of liquid at the distal opening, contact of the globule with the first liquid defining the microfluidic pattern to establish the liquid bridge, and subsequent collapse of the liquid bridge, thereby providing a pulsatile flow, as a result of a pulsatile pressure generated by the cyclical process, of liquid into the microfluidic pattern.

Embodiments of the invention will now be described, by way of example only, with reference to the accompanying drawings in which corresponding reference symbols indicate corresponding parts, and in which.

The Figures are provided for explanatory purposes only and are not depicted to scale in order to allow different elements to be visualised clearly. In particular, in practice it is expected that the widths of the elongate conduits relative to the diameters of reservoirs will be significantly smaller than shown in the Figures.

Figure 1:
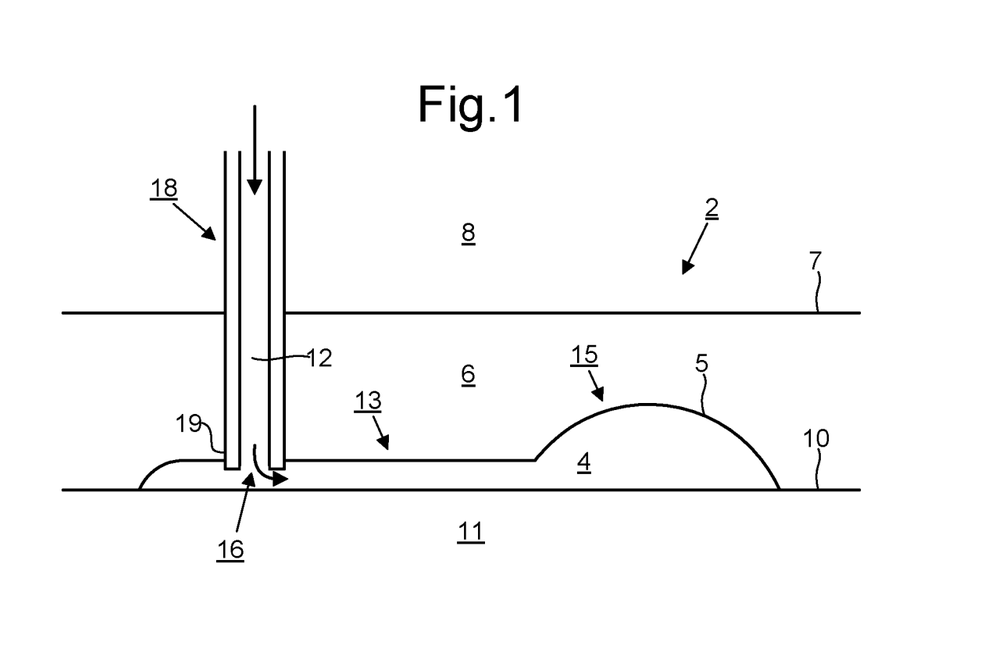
FIG. 1 is a schematic side view depicting pumping of liquid into an elongate conduit of a microfluidic pattern.

Embodiments of the disclosure, as illustrated in FIG. 1, comprise a method of driving flow in a microfluidic arrangement 2. The microfluidic arrangement 2 comprises a first liquid 4. The first liquid 4 is held predominantly by surface tension in a shape defining a microfluidic pattern on a surface 10 of a substrate 11. The microfluidic pattern, formed by the first liquid 4, comprises at least an elongate conduit 13 and a first reservoir 15, as depicted in FIG. 1. In other embodiments the microfluidic pattern may comprise further reservoirs and/or further elongate conduits.

Figure 2:
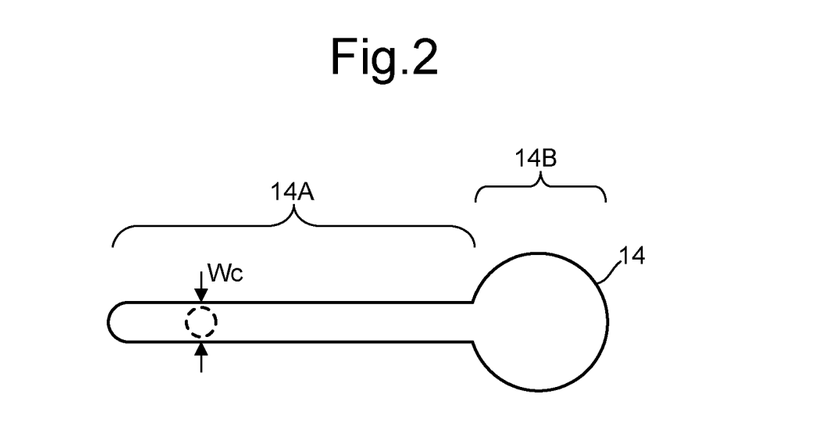
FIG. 2 depicts a conduit footprint and a first reservoir footprint for the arrangement of FIG. 1.

FIG. 2 depicts an area of contact 14 between the microfluidic pattern of FIG. 1 and the substrate 11, viewed from above the substrate 11 (in a direction perpendicular to the surface 10 of the substrate 11). An area of contact 14 between the substrate 11 and a portion of the first liquid 4 that forms the elongate conduit 13 defines a conduit footprint 14A. An area of contact between the substrate 11 and a portion of the first liquid 4 that forms the first reservoir 15 defines a first reservoir footprint 14B. The conduit footprint 14A may have an average length to width aspect ratio of at least 3:1, optionally at least 5:1, optionally at least 10:1, for example. The first reservoir footprint 14B will typically not be elongate to any significant degree. The first reservoir footprint 14B may for example be substantially circular or, if not circular, have an average length to width aspect ratio of less than 3:1, optionally less than 2:1.

Typically, the surface 10 will be substantially planar and unpatterned (neither mechanically nor chemically), at least in the region of the microfluidic pattern. Thus, the conduit footprint 14A and the first reservoir footprint 14B may be wholly provided on a substantially planar portion (which may be provided at any angle relative to the horizontal or to any other portion of the substrate 11) and/or substantially unpatterned portion of the surface 10 of the substrate 11. A region of the surface 10 of the substrate 11 outside of microfluidic pattern may thus be indistinguishable from the region of the surface 10 that is in contact with the microfluidic pattern.

As depicted in FIG. 1, a delivery member 18 having an internal lumen 12 is provided (e.g. a hollow needle). The internal lumen 12 leads to a distal opening 16 through which liquid can be delivered. Liquid is pumped into the microfluidic pattern while the distal opening is held in a delivery position. The liquid is pumped from outside of the microfluidic pattern into the microfluidic pattern via the distal opening 16. FIG. 1 depicts a delivery member 18 in an example delivery position. The delivery position is generally such that the liquid enters the microfluidic pattern via the elongate conduit 13 and drives a flow of liquid into the first reservoir 15. An example region of entry of the liquid relative to the conduit footprint 14A is depicted in FIG. 2 by the broken line circle. The driving of the flow of liquid into the first reservoir 15 is desirably achieved without any change in the shape of the area of contact 14 between the microfluidic pattern and the substrate 11.

As explained above, pumping liquid into the elongate conduit 13 rather than into a larger structure enables higher pressures to be achieved in the region of injection of liquid, facilitating the establishment of larger pressure gradients within the microfluidic pattern and therefore higher flow rates. The maximum Laplace pressure achievable within the elongate conduit 13 without causing de-pinning of the walls of the elongate conduit 13 (and therefore a change in shape of the conduit footprint 14A), is determined by the width of the conduit. It is generally desirable to make the width of the conduit relatively small in comparison with the diameter or diameters of the reservoir or reservoirs into which a flow of liquid is to be driven. In embodiments such as that of FIG. 1, the size and shape of each of the conduit footprint 13 and the first reservoir footprint 15 are preferably such that a maximum Laplace pressure supportable by the first liquid 4 in the elongate conduit 13 without any change in the conduit footprint 14A is higher than a maximum Laplace pressure supportable by the first liquid 4 in the first reservoir 15 without any change in the first reservoir footprint 14B.

Figure 3:
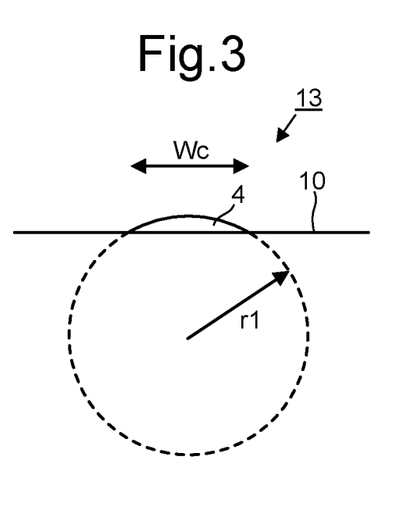
FIG. 3 is an end sectional view along an elongate conduit depicting a relatively low curvature associated with a relatively low pressure difference across the interface defining the elongate conduit.
Figure 4:
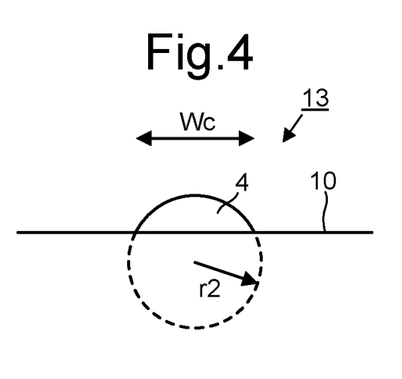
FIG. 4 depicts the conduit of FIG. 3 with a larger pressure difference across the interface.

FIGS. 3 and 4 are end sectional views along an axis of elongation of the elongate conduit 13. The width We of the elongate conduit 13 is within the plane of the page. A Laplace pressure within the elongate conduit 13 depends on the curvature of the interface between the first liquid 4 in the elongate conduit 13 and the fluid above the elongate conduit 13. FIG. 3 illustrates a case where the curvature of the interface is relatively small (illustrated by the relatively large radius of curvature r1 of a complete circle formed by extending the interface as shown by the broken line). The Laplace pressure can be increased by pumping liquid into the elongate conduit 13, which will result in the radius of curvature reducing. This can be done without changing the conduit footprint as long as the radius of curvature does not become so small that the elongate conduit 13 becomes unstable. The elongate conduit 13 with a higher Laplace pressure is depicted schematically in FIG. 4, where the radius of curvature r2 of the broken line circle is significantly smaller than the radius of curvature r1 of FIG. 3. Any attempt to increase the pressure further will cause the elongate conduit 13 to widen, thereby changing the conduit footprint 14A. The maximum Laplace pressure obtainable for given fluids either side of the interface of the elongate conduit 13 will in general depend on the width of the elongate conduit 13, with smaller widths normally allowing higher maximum Laplace pressures to be reached. The flow rate into a reservoir from the elongate conduit 13 depends on the pressure difference between the elongate conduit 13 and the reservoir, which in turn depends on the rate at which fluid is injected into the elongate conduit 13 (which contributes to the pressure in the elongate conduit 13) and the curvature of the reservoir. Hydrostatic pressure may also contribute to the pressure difference where the height of the elongate conduit 13 is different to the height of the reservoir, but this is likely to be a small effect when liquid is being actively pumped into the elongate conduit 13.

Figure 5:
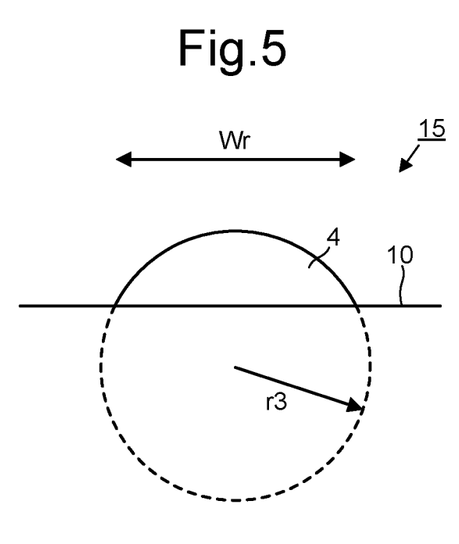
FIG. 5 is a sectional view through a reservoir showing a maximum curvature supportable by the reservoir.

FIG. 5 is a sectional view through the first reservoir 15 showing a geometry corresponding to a maximum Laplace pressure that is achievable within the first reservoir 15. The much larger width Wr across the first reservoir 15 (which in practice will be significantly greater than twice the width We across the elongate conduit 13) means that the corresponding maximum Laplace pressure is significantly lower than is achievable within the elongate conduit 13 (radius r3 will be significantly greater than twice the radius r2).

In an embodiment, as depicted in FIG. 1, the microfluidic arrangement further comprises a second liquid 6. The second liquid 6 is in direct contact with the first liquid 4 and covers all of the microfluidic pattern. Thus the first liquid 4 of the microfluidic pattern may be in contact exclusively with a planar unpatterned surface 10 below and with the second liquid 6 along all of the rest of the outer interface of the first liquid 4. The second liquid 6 isolates the first liquid 4 from the surrounding environment 8 (e.g. air). The second liquid 6 may therefore reduce or prevent evaporation of the first liquid 4. The second liquid 6 reduces or prevents contamination of the first liquid 4. The second liquid 6 is substantially immiscible with the first liquid 4.

The delivery position of the delivery member 18 is preferably below an upper interface 7 of the second liquid 6. The distal opening 16 is thus always sealed from the environment (e.g. air) outside of microfluidic arrangement. As discussed above, the delivery position may be such that the distal opening 16 would be above or below an interface 5 between the first liquid 4 and the second liquid 6 in the absence of pumping from the distal opening 16.

In an embodiment, at least a selected portion 19 of the outer surface of the delivery member 18 proximate to the distal opening 16 is configured such that a surface energy density (surface energy per unit area) is lower in respect of contact with the first liquid 4 than in respect of contact with the second liquid 6. It is therefore energetically more favourable for the first liquid 4 to wet the delivery member 18 than for the second liquid 6 to wet the delivery member 18. In the case where the first liquid 4 contains a high proportion of water, the selected portion 19 of the outer surface may be configured to be hydrophilic for example. Configuring the delivery member in this way helps to provide efficient insertion and sealing of the delivery member 18 into the microfluidic pattern. In an embodiment, the selected portion 19 forms a closed ring around the delivery member 18. The selected portion 19 may comprise an end surface of the delivery member, a side surface of the delivery member, or both. The selected portion 19 may comprise a region that is directly adjacent to the distal opening 16. The selected portion 19 may be partially or completely implemented by treating a surface of the delivery member 18, for example by coating, or by providing a delivery member comprising an inner element and a sleeve over the inner element, wherein an outer surface of the sleeve provides the selected portion 19.

Figure 6:
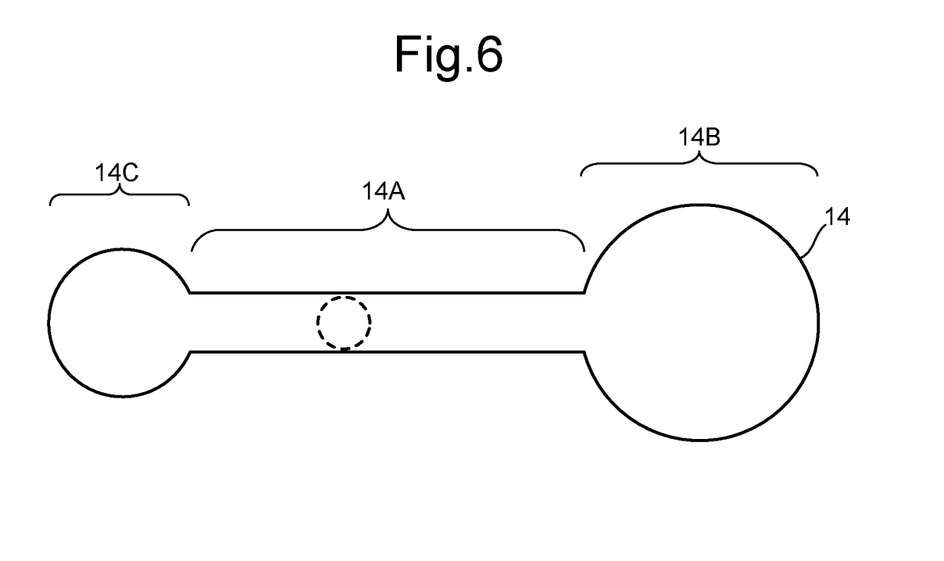
FIG. 6 depicts footprints in a microfluidic arrangement comprising two reservoirs connected to each other by an elongate conduit.

In various embodiments, the microfluidic pattern comprises one or more further reservoirs and the pumping of liquid into the microfluidic pattern drives flow of liquid into a first reservoir and the one or more further reservoirs. FIG. 6 depicts an area of contact 14 between an example microfluidic pattern of this type and the substrate 11. As before, the area of contact 14 comprises a conduit footprint 14A and a first reservoir footprint 14B. The area of contact 14 additionally comprises a further reservoir footprint 14C. More than one further reservoir could be provided, in which case there would be corresponding additional further reservoir footprints. The sizes of the different reservoirs can be chosen to control flow rate into them. In the example shown in FIG. 6, the first reservoir footprint 14B is larger than the further reservoir footprint 14C, which would result in a flow rate into the first reservoir being on average higher than a flow rate into the further reservoir. A Laplace pressure in the first reservoir will rise more slowly as a function of the amount of liquid that has been pumped into it than the further reservoir. Alternatively or additionally, the relative rate of flow of liquid into the different reservoirs can be controlled by appropriate selection of where liquid is injected into the elongate conduit 13. In particular, a rate of flow into a given reservoir can generally be increased by injecting liquid into the elongate conduit 13 at a position that is closer to that reservoir.

Figure 7:
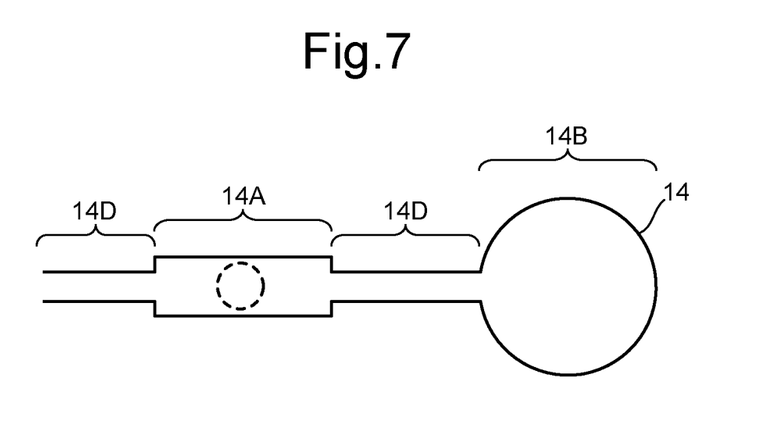
FIG. 7 depicts footprints in a microfluidic arrangement in which an elongate conduit is provided with a localized region of increased width.

In the embodiments described above, the geometry of the elongate conduit 13 comprises an elongate element of constant width. In other embodiments the elongate conduit 13 may have more complex geometries. For example, a conduit may be provided in which a width varies along the length of the conduit. In this case the conduit may be considered to comprise a plurality of elongate conduits 13 in series, wherein at least two of the elongate conduits 13 have different widths relative to each other. In such an embodiment, the delivery position should still be such that the liquid enters the microfluidic pattern via one of the elongate conduits 13 available. FIG. 7 depicts an area of contact 14 between an example microfluidic pattern of this type and the substrate 11. The area of contact 14 comprises a conduit footprint 14A and a first reservoir conduit 14B as before, together with two further conduit footprints 14D. The provision of elongate conduits 13 of different width may make it easier to position the delivery member to pump liquid into the microfluidic pattern, by providing the option to select an elongate conduit 13 of slightly larger width (as exemplified by the region of entry of the liquid depicted by broken line circle in FIG. 7).

Figure 8:
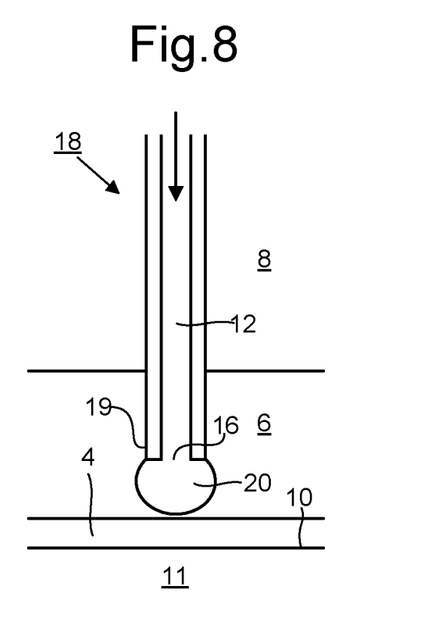
FIG. 8 is a schematic side view depicting growth of a globule of liquid at the distal opening of a delivery member.
Figure 9:
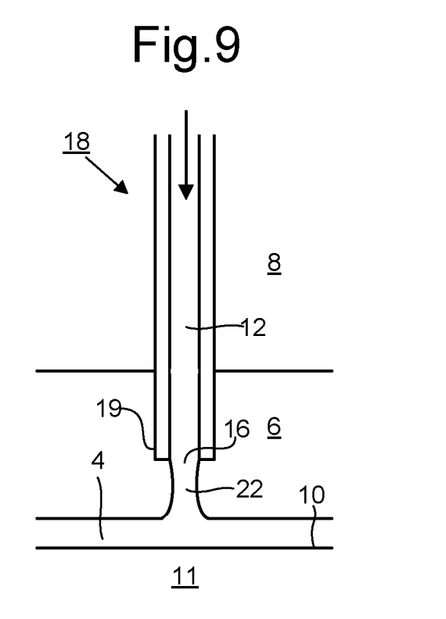
FIG. 9 depicts a liquid bridge formed when the globule of FIG. 8 contacts the first liquid.

FIGS. 8 and 9 depict an embodiment in which the delivery position is such that the delivery member 18 would not be in contact with the elongate conduit 13 in the absence of any flow of liquid out of the distal opening 16. In such embodiments, the liquid is pumped into the elongate conduit 13 via a liquid bridge 22 formed between the distal opening 16 and the elongate conduit 13 by a flow of liquid out of the distal opening 16. As depicted in FIG. 8, the flow of liquid out of the distal opening 16 initially causes growth of a globule 20 of liquid. Where a second liquid 6 is provided, the globule 20 will typically have a composition that is more similar to the composition of the first liquid 4 than to the composition of the second liquid 6 (e.g. both may be aqueous). The liquid forming the globule 20 will typically be substantially immiscible with the second liquid 6. As shown in FIG. 9, when the globule grows sufficiently that it contacts the first liquid 4 a liquid bridge 22 forms between the liquid in the delivery member 18 and the first liquid 4 in the microfluidic pattern. The liquid bridge 22 allows liquid to be pumped into the microfluidic pattern from the delivery member 18.

In an embodiment, the delivery position and pumping are configured so that during a period of uninterrupted flow out of the distal opening 16 a stable liquid bridge 22 is maintained between the distal opening 16 and the elongate conduit 13. Thus, the liquid bridge 22 is present during all of the period of uninterrupted flow A corresponding uninterrupted flow of liquid into the elongate conduit 13 is thereby provided.

In other embodiments, the delivery position and pumping are configured so that during a period of uninterrupted flow out of the distal opening 16 an unstable liquid bridge 22 is periodically formed in a cyclical process comprising growth of a globule 20 of liquid at the distal opening 16, contact of the globule 20 with the elongate conduit 13 to establish the liquid bridge 22, and subsequent collapse of the liquid bridge 22. A pulsatile flow of liquid into the elongate conduit 13 is thereby provided. The pulsatile flow can be achieved even when a substantially constant flow rate is provided to the distal opening 16. A relatively simple pumping arrangement can therefore be used (e.g. suitable for providing a constant flow) to achieve a regular pulsatile flow within the microfluidic pattern. Experiments which require pulsatile flow, for example experiments in which it is desirable to imitate conditions within humans or animals, can therefore be realised cheaply and conveniently.

It is particularly desirable in embodiments where a liquid bridge 22 is used to arrange at least a selected portion 19 of the outer surface of the delivery member 18 proximate to the distal opening 16 such that a surface energy density is higher in respect of contact with the first liquid 4 than in respect of contact with the second liquid 6. It is therefore energetically more favourable for the second liquid 4 to wet the selected portion of the delivery member 18 than for the first liquid 4 to wet the delivery member 18. In the case where the first liquid 4 contains a high proportion of water, the selected portion 19 may be configured to be hydrophobic for example. Configuring the delivery member in this way prevents unwanted wetting of the delivery member by liquid leaving the distal opening 16, thereby promoting for example reliable formation of a globule 20 that protrudes towards the elongate conduit 13, as depicted in FIG. 8. In an embodiment, the selected portion 19 forms a closed ring around the delivery member 18. The selected portion 19 may comprise an end surface of the delivery member, a side surface of the delivery member, or both. The selected portion 19 may comprise a region that is directly adjacent to the distal opening 16. The selected portion 19 may be partially or completely implemented by treating a surface of the delivery member 18, for example by coating, or by providing a delivery member comprising an inner element and a sleeve over the inner element, wherein an outer surface of the sleeve provides the selected portion 19. In an embodiment, the delivery member 18 comprises a stainless steel inner element and a PTFE sleeve over the inner element.

In various embodiments the first and second liquids are chosen so that the second liquid 6 is denser than the first liquid 4. For example, the first liquid 4 may be aqueous and the second liquid 6 may comprise a fluorocarbon such as FC40 (a transparent fully-fluorinated liquid of density 1.855 g/ml that is widely used in droplet-based microfluidics). Somewhat counter-intuitively, instead of the denser second liquid 6 sinking to the bottom and displacing the first liquid 4, interfacial forces dominate and the aqueous phase remains stuck to the substrate 11. Providing a denser second liquid 6 is advantageous because it helps to provide more constant rates of flow within the microfluidic pattern. Increases in Laplace pressure as reservoirs grow in size are at least partially compensated by a corresponding decrease in hydrostatic pressure acting on the reservoir, as the depth of the second liquid 6 above the reservoir decreases. This helps to reduce the rate at which pressure gradients within the microfluidic pattern reduce during pumping, thereby contributing to more constant flow rates. This may be particularly desirable where the driving of flow in the microfluidic pattern comprises a passive component. For example in embodiments the flow may be driven for a first time period by actively pumping liquid into the microfluidic pattern using the delivery member 18 and for a second time period, subsequent to the first time period, by passive pumping (with the delivery member 18 optionally retracted outside of the microfluidic arrangement during this period).

The solubility of water in FC40 is <7 ppm by weight, so an aqueous first liquid 4 overlaid with a second liquid 6 comprising FC40 exposed to air above the FC40 is stable for days. FC40 has also been shown to isolate the microfluidic pattern effectively from any other microfluidic patterns that are provided nearby, for example on the same substrate 11 and in contact with the same body of second liquid 6 but not in direct contact with each other.

In an embodiment, the first liquid, second liquid and substrate are selected such that an advancing contact angle of the first liquid 4 on the substrate 11 is higher when the microfluidic pattern is overlaid with the second liquid 6 than if the microfluidic pattern were overlaid with air. This is the case for example when the first liquid 4 is aqueous and the second liquid is FC40. In this case the advancing contact angle is increased by about 20°, meaning that about 60% more liquid can be added to reservoirs before the reservoir footprint changes.

Figure 10:
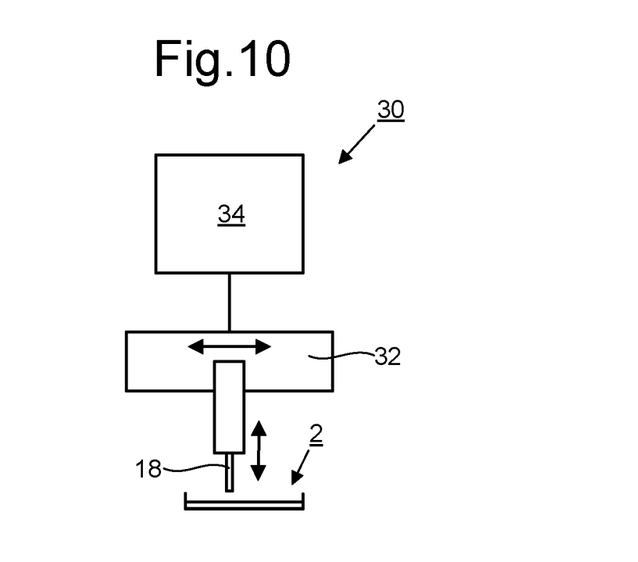
FIG. 10 schematically depicts an apparatus for driving flow in a microfluidic arrangement.

The methods described above may be performed by an apparatus 30 for driving flow in a microfluidic arrangement 2. An example apparatus 30 is depicted schematically in FIG. 10. The apparatus comprises the microfluidic arrangement 2 according to any of the embodiments described above. The apparatus 30 further comprises a pumping mechanism 32 comprising a delivery member 18. The delivery member 18 is moveable by the pumping mechanism 32. A control system 34 controls the pumping mechanism so that a method according to any of the above embodiments can be performed. The control system 34 may control the pumping mechanism for example such that liquid is pumped into the microfluidic pattern while a distal opening 16 of the delivery member 18 is held in a delivery position, the delivery position being such that the liquid enters the microfluidic pattern via an elongate conduit 13 and drives a flow of liquid into a first reservoir 15. Alternatively or additionally, the control system 34 may control the pumping mechanism such that during a period of uninterrupted flow out of the distal opening an unstable liquid bridge is periodically formed in a cyclical process comprising growth of a globule of liquid at the distal opening, contact of the globule with the first liquid defining the microfluidic pattern to establish the liquid bridge, and subsequent collapse of the liquid bridge, thereby providing a pulsatile flow of liquid into the microfluidic pattern.

DETAILED EXAMPLE

Application to Chemotaxis

Chemotaxis requires stable flows, and many microfluidic devices have been developed to study it. As a demonstration of embodiments disclosed herein the inventors constructed a microfluidic pattern comprising a Y-shaped "chemotaxis" circuit, the conduit and reservoir footprints 14A and 14B of which are depicted schematically in FIG. 11. In this example, two elongate conduits were provided, each forming a portion of a different one of the arms of the Y-shape, and leading to a single first reservoir. After printing of the first liquid 4 into the desired pattern, distal openings in two stainless-steel delivery members—filled respectively with blue and red dye and connected to syringes mounted on one pump—were lowered through a second liquid comprising FC40 until they pierce an elongate conduit forming one arm of the Y; the aqueous interface of the first liquid 4 then spontaneously seals around the delivery members (arranged to be hydrophilic in this example). On starting the pump, red and blue dyes are injected into the microfluidic pattern and are observed to flow around right-angle bends (see FIG. 11) at rates up to ~1 ml/h without changing the overall area of contact 14 between the microfluidic pattern and the substrate. If air bubbles are introduced via inlets, buoyancy differences force them to pinch off and be lost to the atmosphere. These results confirm that external pumps can be connected simply through self-sealing "gaskets" to microfluidic patterns as described herein. The fluid interfaces defining the microfluidic pattern are seen to adapt robustly to changing flows, footprints remain unchanged, and the microfluidic arrangement can be operated like counterpart arrangements implemented using solid walled PDMS alternatives, but without problems associated with leaky seals and air bubbles, and general inflexibility.

Figure 11:
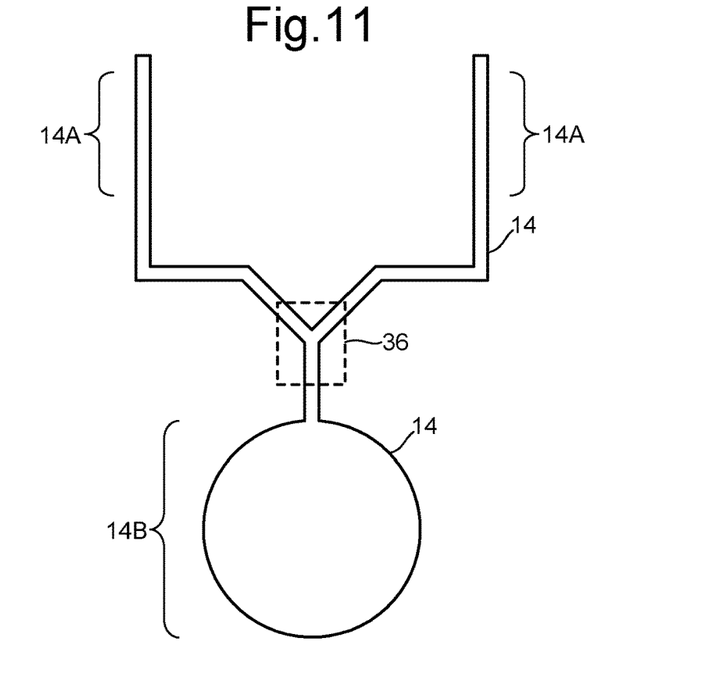
FIG. 11 depicts an area of contact between a microfluidic pattern and a substrate for an example Y-shaped chemotaxis circuit.
Figure 12:
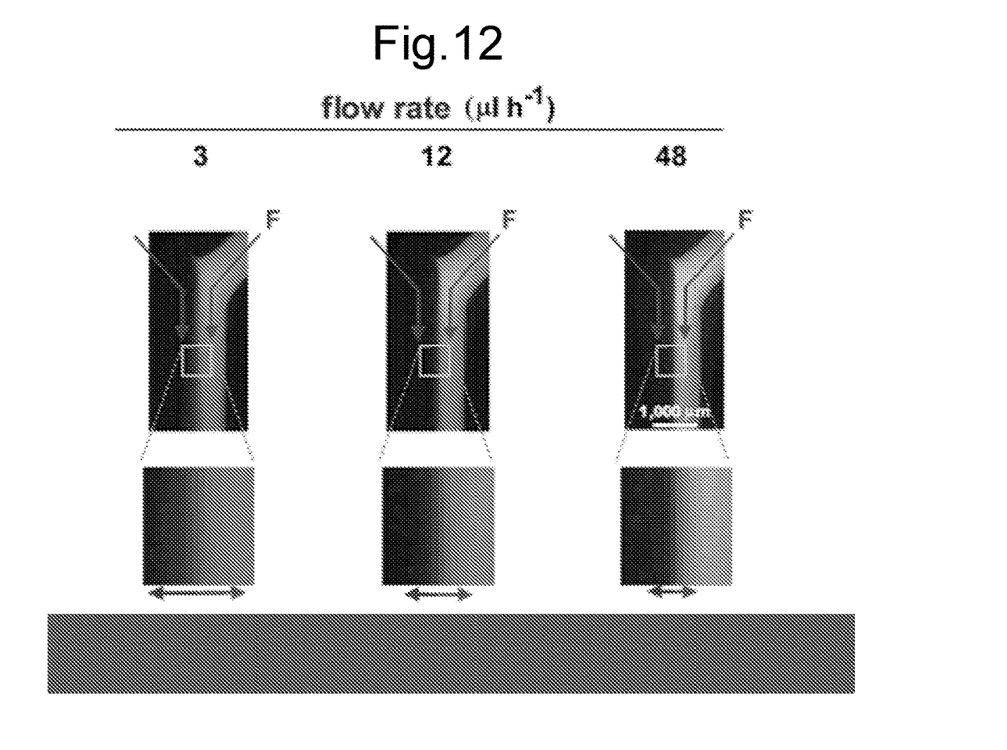
FIG. 12 depicts fluorescent images of the region marked by a broken line box in FIG. 11 during pumping into the circuit of FIG. 11 at three different flow rates.

FIG. 12 depicts images of the region marked 36 in FIG. 11, for three different flow rates of the red and blue dyes. With slow flow, there is time for diffusion to create a gradient, which is seen as blurring between the light and dark regions in the leftmost inset; with fast flow, there is less time and the gradient is steeper (seen as a sharper boundary between the light and dark regions in the rightmost inset). The middle inset shows intermediate blurring for an intermediate flow rate.

The invention claimed is:

1. A method of driving flow in a microfluidic arrangement, wherein
   the microfluidic arrangement comprises a first liquid held predominantly by surface tension in a shape defining a microfluidic pattern on a surface of a substrate, the microfluidic pattern comprising at least an elongate conduit and a first reservoir;
   the area of contact between the substrate and a portion of the first liquid that forms the elongate conduit defines a conduit footprint;
   the area of contact between the substrate and a portion of the first liquid that forms the first reservoir defines a first reservoir footprint;
   the size and shape of each of the conduit footprint and the first reservoir footprint are such that a maximum Laplace pressure supportable by the first liquid in the elongate conduit without any change in the conduit footprint is higher than a maximum Laplace pressure supportable by the first liquid in the first reservoir without any change in the first reservoir footprint; and
   the method comprises: providing a delivery member having an internal lumen leading to a distal opening through which liquid can be delivered; and pumping liquid into the microfluidic pattern through the distal opening while the distal opening is held in a delivery position, the delivery position being such that the liquid enters the microfluidic pattern via the elongate conduit and drives a flow of liquid into the first reservoir.

2. The method of claim 1, wherein the conduit footprint and the first reservoir footprint are wholly on a substantially planar portion of the surface of the substrate.

3. The method of claim 1, wherein the driving of the flow of liquid into the first reservoir is performed without any change in the conduit footprint or the first reservoir footprint.

4. The method of claim 1, wherein the delivery position is such that the delivery member would not be in contact with the elongate conduit in the absence of any flow of liquid out of the distal opening, and wherein the liquid is pumped into the elongate conduit via a liquid bridge formed between the distal opening and the elongate conduit by a flow of liquid out of the distal opening.

5. The method of claim 4, wherein during a period of uninterrupted flow out of the distal opening a stable liquid bridge is maintained between the distal opening and the elongate conduit, thereby providing an uninterrupted flow of liquid into the elongate conduit.

6. The method of claim 4, wherein during a period of uninterrupted flow out of the distal opening an unstable liquid bridge is periodically formed in a cyclical process comprising growth of a globule of liquid at the distal opening, contact of the globule with the elongate conduit to establish the liquid bridge, and subsequent collapse of the liquid bridge, thereby providing a pulsatile flow, as a result of a pulsatile pressure generated by the cyclical process, of liquid into the elongate conduit.

7. The method of claim 1, wherein the microfluidic arrangement further comprises a second liquid in direct contact with the first liquid and covering the microfluidic pattern.

8. The method of claim 7, wherein the delivery position is below an upper interface of the second liquid.

9. The method of claim 7, wherein the first liquid is in contact exclusively with a substantially planar portion of the surface of the substrate and the second liquid.

10. The method of claim 7, wherein the second liquid is denser than the first liquid.

11. The method of claim 7, wherein the first liquid, second liquid and substrate are selected such that an advancing contact angle of the first liquid on the substrate is higher when the microfluidic pattern is overlaid with the second liquid than if the microfluidic pattern were overlaid with air.

12. The method of claim 1, wherein at least a selected portion of the outer surface of the delivery member proximate to the distal opening is configured such that a surface energy density is lower in respect of contact with the first liquid than in respect of contact with the second liquid.

13. The method of claim 1, wherein at least a selected portion of the outer surface of the delivery member proximate to the distal opening is configured such that a surface energy density is higher in respect of contact with the first liquid than in respect of contact with the second liquid.

14. The method of claim 1, wherein the microfluidic pattern comprises one or more further reservoirs and the pumping of liquid into the microfluidic pattern drives flow of liquid into the first reservoir and the one or more further reservoirs.

* * * * *